United States Patent [19]

Candau et al.

[11] Patent Number: 5,603,940
[45] Date of Patent: Feb. 18, 1997

[54] OIL-IN-WATER EMULSION WHICH MAY BE USED FOR OBTAINING A CREAM

[75] Inventors: Didier Candau, Bievres; Pascal Simon, Vitry sur Seine, both of France

[73] Assignee: L'Oreal, Paris, France

[21] Appl. No.: 312,641

[22] Filed: Sep. 27, 1994

[30] Foreign Application Priority Data

Oct. 8, 1993 [FR] France .................. 93 11995

[51] Int. Cl.$^6$ ............... A61K 7/00; B01J 13/00
[52] U.S. Cl. .............. 424/401; 424/70.31; 252/312; 514/939; 514/943
[58] Field of Search ............. 252/312; 424/70.31, 424/401; 514/943, 939

[56] References Cited

U.S. PATENT DOCUMENTS

| | | | |
|---|---|---|---|
| 4,645,794 | 2/1987 | Davis et al. | 525/61 |
| 5,154,855 | 10/1992 | Sekiguchi et al. | 252/312 |
| 5,368,850 | 11/1994 | Cauwet et al. | 424/70.31 |
| 5,534,554 | 7/1996 | Katz et al. | 514/939 |

FOREIGN PATENT DOCUMENTS

0458600A1  11/1991  European Pat. Off. .

OTHER PUBLICATIONS

Patent Abstract of Japan, 01-299233, ABS Grp No: C0690, ABS vol. No. vol. 14, No. 86, ABS Pub Date: Feb. 19, 1990.

*Primary Examiner*—Philip Tucker
*Assistant Examiner*—Daniel S. Metzmaier
*Attorney, Agent, or Firm*—Oblon, Spivak, McClelland, Maier & Neustadt, P.C.

[57] ABSTRACT

The present invention relates to a stable oil-in-water emulsions comprising an oily phase dispersed in an aqueous phase with an emulsifying system. More precisely, the emulsifying system contains a first ester chosen from the fatty acid esters of glucose and the fatty acid esters of alkylglucose and at least one second fatty acid ester of sucrose. The emulsion according to the invention may be used in the cosmetic field and in the field of dermatology in order to obtain a skin cream.

18 Claims, No Drawings

5,603,940

OIL-IN-WATER EMULSION WHICH MAY BE USED FOR OBTAINING A CREAM

FIELD OF THE INVENTION

The present invention relates to a new oil-in-water emulsion of creamy, white and shiny aspect, which is intended in particular for preparing (body, face) skin-care creams and/or creams for face make-up, but also for treating certain skin diseases. If need be, these creams may be coloured using dye in order to produce foundations. These creams are thus intended for cosmetology and dermatology.

The invention also relates to the use of a first and of a second esters as an emulsifying system.

BACKGROUND OF THE INVENTION

It is known for a person skilled in the art to use an emulsifying system in order to stabilize together an aqueous phase and an oily phase, in order thereby to obtain creams in particular. The choice of the emulsifying agents assumes a specific importance for the manufacture of creams that are well-tolerated by the consumer.

Among the emulsifying systems, the use of derivatives of petroleum origin is known. However, although they are not harmful and are suitably tolerated by the skin, these derivatives constitute a starting material, for the preparation of the emulsions, which is non-biodegradable and are dependent on the natural petroleum reserves. Moreover, the use of such derivatives in the manufacture of emulsions results in the use of organic solvents having a toxicity for the skin to a greater or lesser extent.

Japanese Patent JP-A-61271205 discloses a cosmetic composition containing a fatty acid ester of glucose or of sucrose as emulsifying agent. Such an emulsifying agent has the advantage of being better tolerated by sensitive skins than the derivatives from petroleum; it is non-irritant and respects the pH and the hydro-lipid film of the skin. On the other hand, it has the disadvantage of giving creams that are coarse on application to the skin, making them unpleasant for the user.

It is also known (Japanese Patent JP-A-03193210) to use a fatty acid ester of sucrose as emulsifying agent in order to prepare emulsions. However, the use of such agents has the drawback of giving thermally fragile emulsions. Indeed, these agents being more readily susceptible to degrade at temperatures ranging from 50° to 70° C. usually used during the manufacture of emulsions, give caramel-coloured finished products. In addition, this colour develops naturally when these sucrose esters are placed in aqueous solution or in emulsion. This colour becomes considered as a flaw insofar as white products, which are more appreciated by the consumer, are desired above all.

The emulsion according to the invention makes it possible, in particular, to overcome the abovementioned problems. In particular, it has been surprisingly discovered that the combination of at least one first ester chosen from the fatty acid esters of glucose and the fatty acid esters of alkylglucose and at least one second fatty acid ester of sucrose, as emulsifying system in an oil-in-water emulsion, makes it possible to obtain white, shiny creams which are less coarse on application, irrespective of their composition. In addition, this emulsion has the advantage of comprising biodegradable and renewable compounds. Moreover, the temperature for manufacture of this emulsion does not affect the colour, which remains white.

SUMMARY OF THE INVENTION

The invention relates to an oil-in-water emulsion comprising an oily phase which is dispersed in an aqueous phase, and an emulsifying system, the emulsifying system containing at least one first ester chosen from fatty acid esters of glucose and fatty acid esters of alkylglucose, and at least one second fatty acid ester of sucrose.

DETAILED DESCRIPTION OF THE INVENTION AND PREFERRED EMBODIMENTS

The proportions of the aqueous phase may range from 40% to 94% by weight relative to the total weight of the emulsion. The proportions of the oily phase may range from 5% to 50% and preferably from 10% to 30% by weight relative to the total weight of the emulsion. The emulsifying system may represent from 1% to 10% by weight relative to the total weight of the emulsion.

According to a preferred variant, the emulsion may comprise from 66% to 86% by weight of aqueous phase, from 10% to 30% by weight of oily phase, from 4% to 6% by weight of emulsifying system and from 0% to 10% by weight of additives relative to the total weight of the emulsion.

The first ester/second ester ratio by weight is preferably chosen from the ratios ranging from 70/30 to 30/70. This ratio is preferably 50/50. However, ratios ranging from 1/99 to 99/1 may be envisaged.

The first fatty acid ester may be chosen from the compounds obtained by reacting a fatty acid of saturated or unsaturated chain having from 12 to 22 carbon atoms and preferably 16 to 20 carbon atoms with a glucose or with an alkylglucose in which the alkyl group contains from 1 to 6 carbon atoms.

The fatty acid esters of alkylglucose are $C_1$ ethers of glucose in which the alkyl chain comprises from 1 to 6 carbon atoms.

The first fatty acid ester may contain a mixture of mono-, di-, tri- and tetraester derivatives with a proportion which may be of at least 50% by weight of mono- and diester derivatives and not exceeding 95% by weight of monoester derivatives relative to the total weight of the mixture.

The second ester may be chosen from the compounds obtained by reacting a fatty acid of saturated or unsaturated carbon chain having from 12 to 22 carbon atoms and preferably from 16 to 20 carbon atoms with sucrose.

For $C_{11}$ and $C_{10}$ esters, a detergent solution is obtained instead and for $C_{23}$ and $C_{24}$ esters, a rather solid product is obtained.

The second fatty acid ester may contain a mixture of mono-, di-, tri-, tetra- and polyester derivatives with a proportion of monoester derivatives which may range from 30% to 95% by weight relative to the total weight of the mixture.

The first ester may be chosen from glucose palmitate, alkylglucose sesquistearates, for instance methylglucose sesquistearate and alkylglucose palmitates, for instance methylglucose palmitate or ethylglucose palmitate.

The invention also relates to the use of at least one first ester chosen from fatty acid esters of glucose and fatty acid esters of alkylglucose and of at least one second fatty acid ester of sucrose, in an oil-in-water emulsion, as an emulsifying system.

The second ester may be chosen from sucrose palmitostearate, sucrose stearate and sucrose monolaurate.

One or more oils chosen from organopoly-siloxanes, mineral, organic, synthetic or vegetable oils, in particular vaseline, jojoba or sunflower oil, synthetic perhydrosqualene, isostearyl isostearate and isopropyl myristate may be used as oily phase.

The emulsion of the invention may also contain gelling agents chosen from base-neutralized polyacrylic acids and natural gums formed of polysaccharides (guar, xanthan). The proportion of gelling agents represents from 0.01% to 1% by weight relative to the total weight of the emulsion.

The emulsion according to the invention may also contain an additive chosen from hydrating agents (polyols), vitamins, UV filters, preserving agents, fragrances and antioxidants. Among the polyols, glycerol may be used. The proportions of hydrating agents, vitamins and UV filters range respectively from 0.1% to 10% by weight, from 0.1% to 5% by weight and from 0.5% to 5% by weight relative to the total weight of the emulsion.

Other additives may be envisaged, for instance organic or inorganic dyes and co-emulsifying agents. Fatty alcohols having from 12 to 24 carbon atoms and preferably from 16 to 22 carbon atoms may be used as co-emulsifying agents. The proportion of fatty alcohol ranges from 1% to 5% by weight relative to the total weight of the emulsion. Cetyl alcohol, behenyl alcohol and the like may be mentioned as fatty alcohol.

In the case of fatty acid esters of glucose, the fatty acid may be attached to the glucose residue in any of positions $C_2$, $C_3$, $C_4$ or $C_6$. This makes it possible to give a mixture of mono-, di-, tri- and tetraester. This mixture may comprise at least 50% by weight of mono- and diester derivatives, but does not exceed 95% by weight of monoester derivatives relative to the total weight of the mixture. These proportions of these ester derivatives make it possible to obtain an oil-in-water emulsion.

The fatty acid esters of glucose used according to the invention are, for example, chosen from "GLUCATE SS" sold by the company Amerchol, "GRILLOCOSE PS" sold by the company Grillo-Werke, or "BIOSURF 16" sold by the company Novo.

The fatty chain of the fatty acid esters of sucrose is a saturated or unsaturated chain which comprises from 12 to 22 carbon atoms.

The fatty acid may be attached to the sucrose residue in position $C_2$, $C_3$, $C_4$ or $C_6$ of the glucose residue or in position $C_2$, $C_3$, $C_5$ or $C_6$ of the fructose residue. This makes it possible to obtain a mixture of mono-, di-, tri-, tetra- and polyester. The fatty acid esters of sucrose used are, for example, chosen from crodesta F160, F140, F110, F90, F70 and SL40 sold by the company Croda or from the Ryoto sugar esters sold by the company Mitsubishi.

The preferred proportion of the first ester-second ester mixture is approximately 5% by weight relative to the total weight of the emulsion.

The invention also relates to a skin-treating cream containing an emulsion as defined above.

Another subject of the invention is the use of the emulsion defined above for the preparation of a cream intended for treating skin diseases.

Concrete, but in no way limiting, examples of emulsions illustrating the invention will now be given.

In these examples, the emulsions were obtained by incorporating the first and second esters into water possibly containing the hydrophilic additives, then in heating the mixture between 60° C. and 70° C. with stirring for 15 to 45 min. After complete dissolution of the esters the oily phase, heated to 60° C. beforehand and containing the lipophilic additives, is introduced into the aqueous phase. The mixture is then stirred vigorously while maintaining the heating. The mixture is allowed to cool under moderate stirring.

Examples 1 and 2 give white, shiny, smooth emulsions of light application which penetrate easily. After application, the skin is shiny and is hardly at all sticky. The emulsions of these two examples are intended for the care of dry skin-types.

| EXAMPLE 1: | | |
|---|---|---|
| Emulsifying agents | | |
| Methylglucose sesquistearate (GRILLOCOSE PS) | | 3% |
| Sucrose palmitostearate (CRODESTA F160) (73% monoester, 27% di-triester) | | 6% |
| Oily phase | | |
| Vaseline oil | | 20% |
| Isopropyl myristate | | 25% |
| Additives | | |
| Antioxidants (BHT and BHA) | | 0.5% |
| Preserving agents (methyl para-hydroxybenzoate and imidazolidinyl urea) | | 0.1% |
| Co-emulsifyiug agent (cetyl alcohol) | | 1% |
| Water | qs | 100% |
| EXAMPLE 2: Nourishing cream | | |
| Emulsifying agents | | |
| Methylglucose sesquistearate (GRILLOCOSE PS) | | 3.5% |
| Sucrose stearate (CRODESTA F110) (52% monoester, 48% di-triester) | | 1.5% |
| Oily Phase | | |
| Sunflower oil | | 15% |
| Jojoba oil | | 4% |
| Additives | | |
| Lanolin alcohol | | 3% |
| Xanthan gum | | 0.2% |
| Antioxidants (BHT and BHA) | | 0.7% |
| Preserving agents (methylparaben and imidazolidinyl urea) | | 0.2% |
| Co-emulsifying agent (behenyl alcohol) | | 2% |
| Water | qs | 100% |
| EXAMPLE 3: | | |
| Emulsifying agents | | |
| Glucose palmitate (described in French Patent Application No. 92-03811 | | 3% |
| Sucrose palmitostearate (CRODESTA F70) (39% monoester, 61% di-triester | | 7% |
| Oily phase | | |
| Perhydrosqualene | | 5% |
| Isostearyl isostearate | | 13% |
| Additives | | |
| Glycerol | | 3% |
| Antioxidants (BHT and BHA) | | 0.6% |
| Preserving agents (methylparaben and imidazolidinyl urea) | | 0.15% |
| Water | qs | 100% |

The emulsion obtained is white and shiny and is used to protect the skin as in Example 1, while at the same time being less greasy.

EXAMPLE 4:

| Emulsifying agents | |
|---|---|
| Ethylglucose palmitate (BIOSURF 16) | 6% |
| Sucrose monolaurate (CRODESTA SL 40) | 4% |
| Oily phase | |
| Polydimethylsiloxame (ABIL 10 sold by the company Goldschmidt) | 2% |
| Polycetylmethylsiloxane (ABIL WAX 9801 sold by the company Goldschmidt) | 2% |
| Emollient (pure sellin liquid sold by the company Dragoco) | 2% |
| Additives | |
| Antioxidants (BHT and BHA) | 0.55% |
| Preserving agents (methyl para-hydroxybenzoate and imidazolidinyl urea) | 0.05% |
| Water | qs 100% |

Example 4 gives a white and shiny emulsion which is intended for the carea of normal skin-types.

None of the emulsions of Examples 1 to 4 contains a fragrance. Indeed, one of the advantages of the invention is that these emulsions have no unpleasant odour, in contrast with emulsions which comprise petroleum derivatives as emulsifying agent. It is thus not necessary in the emulsions according to the invention to add a fragrance in order to counteract the presence of these unpleasant odours.

The sensory properties of the cream of Example 2 were tested on a panel of 30 expert volunteers. Each person evaluated the cream by making a single application to the face and by completing a questionnaire featuring 19 describers relating to the aspect of the product and to its qualities of hold, spreading, immediate comfort and comfort with time, after one day.

A "counter-example" cream in accordance with the prior art, in which the mixture of esters of glucose and of sucrose (5% by weight in total) is replaced exclusively by glucose ester (5% by weight), was tested under the same conditions.

The coarseness of the creams on application to the skin may be evaluated by the suppleness, waxiness and lightness describers. The cream of Example 2 is judged to be more supple (significance according to the Student test; risk α=0.01%), lighter (significance according to the Student test; risk α=0.01%) and less waxy (significance according to the Student test; risk α=0.01%) than the "counter-example" cream.

The general opinion is also in favour of the cream of Example 2 (confidence interval α=10%); this cream obtains a score of satisfactory opinions which is 16% higher than that of the cream containing the glucose ester exclusively.

We claim:

1. Oil-in-water emulsion comprising an oily phase dispersed in an aqueous phase and an emulsifying system, wherein the emulsifying system comprises at least one first fatty acid ester selected from the group consisting of fatty acid esters of glucose and the fatty acid esters of alkylglucose, wherein said first fatty acid ester contains a mixture of mono-, di-, tri- and tetraester derivatives with a proportion of at least 50% by weight of mono- and diesters derivatives not exceeding 73% by weight of monoester relative to the total weight of the mixture, and at least one second fatty acid ester of sucrose.

2. Emulsion according to claim 1, wherein the aqueous phase represents from 40% to 94% by weight relative to the total weight of the emulsion.

3. Emulsion according to claim 1, wherein the oily phase represents from 5% to 50% by weight relative to the total weight of the emulsion.

4. Emulsion according to claim 1, wherein the emulsifying system represents from 1% to 10% by weight relative to the total weight of the emulsion.

5. Emulsion according to claim 1, wherein the oily phase represents from 10% to 30% by weight relative to the total weight of the emulsion.

6. Oil-in-water emulsion comprising:
   from 66% to 86% of aqueous phase,
   from 10% to 30% of oily phase,
   from 4% to 6% of emulsifying system, and
   from 0% to 10% of additives selected from the group consisting of gelling agents, hydrating agents, vitamins, fragrances, preserving agents and antioxidants,
   wherein the emulsifying system is as in claim 1.

7. Oil-in-water emulsion comprising:
   from 66% to 86% of aqueous phase,
   from 10% to 30% of oily phase,
   from 4% to 10% of emulsifying system,
   wherein the emulsifying system is as in claim 1, and wherein the emulsifying system comprises from 1% to 5% of fatty alcohol by weight of the total composition.

8. Emulsion according to claim 1, wherein the first fatty acid ester/second fatty acid ester ratio is between 70/30 and 30/70.

9. Emulsion according to claim 1, wherein the first fatty acid ester is the compounds obtained by reacting a fatty acid of saturated or unsaturated carbon chain having from 12 to 22 carbon atoms with glucose or with an alkylglucose in which the alkyl group contains from 1 to 6 carbon atoms.

10. Emulsion according to claim 1, wherein the second fatty acid ester is compounds obtained by reacting a fatty acid of saturated or unsaturated carbon chain having from 12 to 22 carbon atoms with sucrose.

11. Emulsion according to claim 10, wherein the second fatty acid ester contains a mixture of the mono-, di-, tri-, tetra- and polyester derivatives with a proportion of monoester derivatives ranging from 30% to 95% by weight relative to the total weight of the mixture.

12. Emulsion according to claim 1, wherein the first ester is selected from the group consisting of methylglucose sesquistearate, ethylglucose palmitate, methylglucose palmitate and glucose palmitate.

13. Emulsion according to claim 1, wherein the second ester is selected from the group consisting of sucrose palmitostearate, sucrose stearate and sucrose monolaurate.

14. A cream for treating the skin, comprising an emulsion according to claim 1.

15. A method for treating skin diseases, comprising applying to skin in need of such treatment a cream comprising the emulsion according to claim 1.

16. A method for emulsifying an oily material in water to prepare an oil-in-water emulsion, comprising emulsifying an oily material with an emulsifier selected from the group consisting of at least one first ester selected from the group consisting of fatty acid esters of glucose and fatty acid esters of alkylglucose, wherein said first fatty acid ester contains a mixture of mono-, di-, tri- and tetraester derivatives with a proportion of at least 50% by weight of mono and diesters derivatives not exceeding 73% by weight of monoester relative to the total weight of the mixture, and at least one second fatty acid ester of sucrose.

17. The method according to claim 16, wherein the first fatty acid ester is compounds obtained by reacting a fatty acid of saturated or unsaturated carbon chain having from 12 to 22 carbon atoms with glucose or with an alkylglucose in which the alkyl group contains from 1 to 6 carbon atoms.

18. The method according to claim 16, wherein the second fatty ester is compounds obtained by reacting a fatty acid of saturated or unsaturated carbon chain having from 12 to 22 carbon atoms with sucrose.

* * * * *